US010258758B1

(12) United States Patent
Faram et al.

(10) Patent No.: US 10,258,758 B1
(45) Date of Patent: Apr. 16, 2019

(54) FLOW CONTROLLED VALVE FOR A SMALL-VOLUME NEBULIZER (71) Applicant: Caddo Medical Technologies LLC, Dallas, TX (US)

(72) Inventors: Joseph Dee Faram, Dallas, TX (US); Evan Dyer Faram, Dallas, TX (US)

(73) Assignee: Caddo Medical Technologies LLC, Dallas, TX (US)

(*) Notice: Subject to any disclaimer, the term of this patent is extended or adjusted under 35 U.S.C. 154(b) by 0 days.

(21) Appl. No.: 15/958,369

(22) Filed: Apr. 20, 2018

(51) Int. Cl.
*A61M 16/20* (2006.01)
*A61M 16/08* (2006.01)
*A61M 15/00* (2006.01)
*A61M 15/06* (2006.01)

(52) U.S. Cl.
CPC .... *A61M 16/0833* (2014.02); *A61M 15/0013* (2014.02); *A61M 15/0021* (2014.02); *A61M 15/002* (2014.02); *A61M 15/0028* (2013.01); *A61M 15/06* (2013.01)

(58) Field of Classification Search
CPC .......... A61M 16/0833; A61M 15/0021; A61M 15/06; A61M 15/002; A61M 15/0028
USPC ............................................................ 482/13
See application file for complete search history.

(56) References Cited

U.S. PATENT DOCUMENTS

| | | |
|---|---|---|
| 2,726,896 A | 12/1955 | McKinnon |
| 3,172,406 A | 3/1965 | Bird et al. |
| 3,762,409 A | 10/1973 | Lester |
| 3,774,602 A | 11/1973 | Edwards |
| 3,945,378 A | 3/1976 | Paluch |
| 4,036,919 A | 7/1977 | Komendowski et al. |
| 4,150,071 A | 4/1979 | Pecina |
| 4,253,468 A | 3/1981 | Lehmbeck |
| 4,261,354 A | 4/1981 | Nelson |
| 4,534,343 A | 8/1985 | Nowacki et al. |
| 4,595,002 A | 6/1986 | Michaels et al. |
| 4,657,007 A | 4/1987 | Carlin et al. |
| 4,951,661 A | 8/1990 | Sladek |
| 5,012,804 A | 5/1991 | Foley et al. |
| 5,027,809 A | 7/1991 | Robinson |
| 5,337,962 A | 8/1994 | Erb et al. |
| 5,357,945 A | 10/1994 | Messina |
| 5,364,615 A | 11/1994 | Debs et al. |

(Continued)

FOREIGN PATENT DOCUMENTS

| | | |
|---|---|---|
| EP | 1417982 A2 | 5/2004 |
| GB | 2055307 A | 3/1981 |

(Continued)

OTHER PUBLICATIONS

Robert M. Kacmarek, Humidity and Aerosol Therapy, Foundations of Respiratory Care, 1992, pp. 793-824, Churchill Livingstone Inc., New York, United States.

(Continued)

*Primary Examiner* — Timothy A Stanis
(74) *Attorney, Agent, or Firm* — Hitchcock Evert LLP

(57) ABSTRACT

The invention relates to a flow controlled valve system. The flow controlled valve may be incorporated into a pre-filled, small-volume nebulizer assembly with a T-connector. The flow controlled valve allows different airflow characteristics in each direction. The flow controlled valve also facilitates breathing physiotherapy by creating different airflow resistances during inhalation and exhalation.

20 Claims, 8 Drawing Sheets

(56) References Cited

U.S. PATENT DOCUMENTS

| | | | |
|---|---|---|---|
| 5,429,122 A | 7/1995 | Zanen et al. | |
| 5,490,630 A | 2/1996 | Hecker | |
| 5,579,757 A | 12/1996 | McMahon et al. | |
| 5,584,285 A | 12/1996 | Salter et al. | |
| 5,727,542 A | 3/1998 | King | |
| 5,813,401 A | 9/1998 | Radcliff et al. | |
| 5,823,179 A | 10/1998 | Grychowski et al. | |
| 5,826,570 A | 10/1998 | Goodman et al. | |
| 5,864,097 A | 1/1999 | Alvino | |
| 6,044,841 A | 4/2000 | Verdun et al. | |
| 6,257,231 B1 | 7/2001 | Shick et al. | |
| 6,355,002 B1 | 3/2002 | Faram et al. | |
| 6,363,932 B1 | 4/2002 | Forchione et al. | |
| 6,390,090 B1 | 5/2002 | Piper | |
| 6,412,481 B1 | 7/2002 | Bienvenu et al. | |
| 6,422,234 B1 | 7/2002 | Bacon | |
| 6,510,846 B1 | 1/2003 | O'Rourke | |
| 6,527,011 B1 * | 3/2003 | Mantz | A61M 16/208 128/203.11 |
| 6,632,842 B2 | 10/2003 | Chaundry et al. | |
| 6,663,574 B2 | 12/2003 | Faram et al. | |
| 6,679,250 B2 | 1/2004 | Walker et al. | |
| 6,722,364 B2 | 4/2004 | Connelly et al. | |
| 6,923,175 B2 | 8/2005 | Poole et al. | |
| 6,994,083 B2 | 2/2006 | Foley et al. | |
| 7,191,780 B2 | 3/2007 | Faram | |
| 7,204,245 B2 * | 4/2007 | Johnson | A61M 15/0086 128/200.14 |
| 7,267,120 B2 | 9/2007 | Rustad et al. | |
| 7,802,568 B2 | 9/2010 | Eicher et al. | |
| 7,909,033 B2 | 3/2011 | Faram | |
| 8,051,854 B2 | 11/2011 | Faram | |
| 8,539,951 B1 | 9/2013 | Meyer et al. | |
| 9,050,434 B2 | 6/2015 | Faram | |
| 9,151,425 B2 | 10/2015 | Faram | |
| 9,566,397 B2 | 2/2017 | Faram | |
| 9,849,254 B2 | 12/2017 | Faram | |
| 2001/0022279 A1 | 9/2001 | Denyer et al. | |
| 2002/0162554 A1 | 11/2002 | Loescher | |
| 2004/0031485 A1 | 2/2004 | Rustad et al. | |
| 2005/0217666 A1 | 10/2005 | Fink et al. | |
| 2006/0021613 A1 | 2/2006 | Overlander | |
| 2008/0078383 A1 | 4/2008 | Richards et al. | |
| 2009/0050141 A1 | 2/2009 | King et al. | |
| 2009/0188500 A1 | 7/2009 | Faram | |
| 2009/0217923 A1 * | 9/2009 | Boehm | A61M 11/06 128/200.14 |
| 2009/0272820 A1 | 11/2009 | Foley et al. | |
| 2010/0095958 A1 | 4/2010 | King et al. | |
| 2011/0100360 A1 | 5/2011 | Faram | |
| 2011/0209700 A1 | 9/2011 | Kreutzmann et al. | |
| 2018/0071464 A1 | 3/2018 | Faram | |

FOREIGN PATENT DOCUMENTS

| | | |
|---|---|---|
| JP | 56-66345 | 6/1981 |
| JP | 08-508671 A | 9/1996 |
| JP | 2004-535845 A | 12/2004 |
| JP | 2005-520641 A | 7/2005 |
| WO | 199520989 A1 | 9/1996 |
| WO | 2002055142 A2 | 7/2002 |
| WO | 2003080149 A2 | 10/2003 |
| WO | 2006006963 A2 | 1/2006 |
| WO | 2008144358 A1 | 11/2008 |
| WO | 2011080761 A1 | 7/2011 |

OTHER PUBLICATIONS

Colin Reisner, Joseph Lee, Arthur Kotch, and Gregory Dworkin, Comparison of Volume Output from Two Different Continuous Nebulizer Systems, Annals of Allergy, Asthma & Immunology, Feb. 1996, pp. 209-213, vol. 76.

Harriet Meyer, Antibacterial Agent in Some Asthma Medications Linked to Airway Constriction, UF Scientists Find, UF News, Jan. 11, 2001, pp. 1-2.

James B. Fink and Rajiv Dhand, Aerosol Therapy, Respiratory Care Clinics of North America, Jun. 2001, pp. 131-340, vol. 7, No. 2, W.B. Saunders Company, A Harcourt Health Sciences Company, Philadelphia, United States.

James B. Fink and Bruce K. Rubin, Aerosol Therapy for Children, Respiratory Care Clinics of North America Aerosol Therapy, Jun. 2001, pp. 175-213, vol. 7, No. 2, W.B. Saunders Company, A Harcourt Health Sciences Company, Philadelphia, United States (article from Fink book above).

U.S. Department of Health and Human Services, Food and Drug Administration, Center for Drug Evaluation and Research (CDER), Center for Biologics Evaluation and Research (CBER), Container Closure Systems for Packaging Human Drugs and Biologics Questions and Answers, Guidance for Industry, May 2002, pp. 1-6, United States.

Julie Applyby, I Will Breathe Easier: Safety Concerns Grow Over Pharmacy-Mixed Drugs, 2005, pp. 1-5, USA Today, United States.

Matthew Grissinger, Errors in the Making: Nearly Unreadable Labeling of Plastic Ampules for Nebulizing Agents, Medication Errors, P&T Journal, May 2005, vol. 30, No. 5, pp. 255-258.

Jamalvi SW, Raza SJ, Naz F, Shamim S, and Jamalvi SM, Management of Acute Asthma in Children Using Metered Dose Inhaler and Small Volume Nebulizer, J Pak Med Association, Dec. 2006, 1 page, PubMed.

Chatburn RL and McPeck M., A New System for Understanding Nebulizer Performance, Respir Care, Aug. 2007, 1 page, PubMed.

Catherine A. O'Malley et al., A Day in the Life of a Nebulizer: Surveillance for Bacterial Growth in Nebulizer Equipment of Children With Cystic Fibrosis in the Hospital Setting, Respiratory Care, Mar. 2007, pp. 258-262, vol. 52, No. 3.

Hoisington ER, Chatburn RL, and Stoller JK, A Comparison of Respiratory Care Workload with 2 Different Nebulizers, Respir Care, Apr. 2009, 1 page, PubMed.

Official Action issued for Japanese Patent Application No. 2010-508563, Mailing No. 80146, dated Feb. 20, 2015, 6 pages (translation included).

\* cited by examiner

FLOW CONTROLLED VALVE FOR A SMALL-VOLUME NEBULIZER

FIELD OF THE DISCLOSURE

The invention relates generally to the field of valves which may be used with small-volume nebulizer breathing assemblies.

BACKGROUND

Valves are used in various applications. For example, U.S. Pat. No. 9,566,397, issued Feb. 14, 2017, disclose a small-volume nebulizer with a one-way valve in the T component that facilitates airflow from a nebulizer to a patient during inhalation and seals the nebulizer output to stop airflow from the nebulizer during exhalation. The '397 Patent is incorporated herein by reference.

SUMMARY

The present disclosure teaches a flow controlled valve that allows different air-flow characteristics in each direction.

Some embodiments of the present disclosure provide an apparatus with a pre-filled, small-volume nebulizer combined with a T component and including a flow restrictor having a flow controlled valve. The pre-filled, small-volume nebulizer may include a siphon, a jet and a baffle within a housing. A unit-dose of medication may be also contained within the housing by an inlet port seal. The nebulizer may also include an output seal at the top of the nebulizer body. Alternatively, seals may be located on a patient interface port and the flow restrictor of the T-connector to prevent medicine from escaping the nebulizer.

In such an embodiment, the T component includes a horizontal tube (or patient interface tube) having two ends and a vertical tube. The horizontal tube may have a patient interface port with a mouthpiece and a second port with a flow restrictor in some embodiments. The first port may alternatively be operable to connect to a patient interface component, such as a mouthpiece, mask or other component. The second port may be operable to connect to a flow restrictor and another component, such as a filter, a ventilator circuit or other component. In some embodiments, the T-connector includes a valve configured to open during a user's inhalation and close during a user's exhalation. When closed, the valve may seal against a valve seat within the vertical tube. Some valve embodiments use a flexible membrane held by a connector around the center of the valve.

In some embodiments, the flow restrictor is a flow controlled valve having an opening through which air may flow in both directions. The flow controlled valve also includes a one-way valve section. When air flows in a first direction, the flow controlled valve allows air through the opening and the one-way valve section. When air flows in a second direction, the flow controlled valve allows air through the opening but prevents air flowing through the one-way valve section.

The flow controlled valve may include a strut or brace extending between two points on a valve seat leaving open sections between the strut's sides and the valve seat. The strut may include a hole through the middle that also passes through a valve gate. The hole allows airflow in both directions through the flow controlled valve. The valve gate is attached to said strut and is able to flex from a first position to a second position. In the first position, the valve gate flexes open to allow air to flow around the valve gate through the open sections. In the second position, the valve gate abuts the valve seat, creating a seal that prevents airflow through the open sections.

Some embodiments include another strut located on the valve gate's opposite side. In such embodiments, the hole may pass through both struts and the valve gate. The struts may be aligned or offset from each other.

In some T component embodiments, the flow controlled valve is integrated into the T component. In other embodiments, the flow controlled valve is attached to a T component's port. In such embodiments, the flow controlled valve may be attached by a threaded connection, a fitted connection, a snap fitting, an adhesive connection, sonic welding or other connection.

The flow controlled valve in T component embodiments may be configured to open outward in some embodiments allowing open airflow out of the T component. In such a configuration, the one-way valve will not let airflow inward, thereby restricting the inward airflow to the hole through the flow controlled valve. During use as a respiratory component in this configuration, a patient will have little resistance during exhalation but will be restricted during inhalation.

In other embodiments, the flow controlled valve in T component embodiments may be configured to open inward, allowing open airflow into the T component. In such a configuration, the one-way valve will not let airflow outward, thereby restricting the outward airflow to the hole through the flow controlled valve. During use as a respiratory component in this configuration, a patient will have little resistance during inhalation but will be restricted during exhalation.

In some embodiments, the flow controlled valve may have a duckbilled valve design. The duckbill valve may include a fixed hole through the duckbill valve to allow airflow in both directions. In some embodiments, the fixed hole is located in the duckbill valve's lips. The duckbill valve's lips are closed, except for the fixed hole, when airflow is in a first direction. When airflow moves in the second direction, the lips open creating a larger opening than the fixed hole. Accordingly, while the flow controlled valve allows airflow in both directions, it creates distinct airflow characteristic depending on the flow direction.

In some embodiments, the flow controlled valve may be configured to open inward. In other embodiments, the flow controlled valve may be configured to open outward.

In some embodiments, the flow controlled valve may be a conical-shaped valve with the fixed hole proximate to the point section of the cone shape. The sides of the cone may include one or more valve gates, which open when air moves in one direction and close against struts forming the conical structure when air moves in a second direction.

Additional aspects, advantages and features are included in the following description of exemplary examples thereof, which description should be taken in conjunction with the accompanying figures, wherein like numerals are used to describe the same feature throughout the figures. All patents, patent applications, articles and other publications referenced herein are hereby incorporated herein in their entirety for all purposes.

A BRIEF DESCRIPTION OF THE DRAWINGS

Embodiments will now be described, by way of example only, with references to the accompanying drawings in which.

DETAILED DESCRIPTION

While this invention may be embodied in many different forms, there will herein be described in detail preferred embodiments of the invention with the understanding that the present disclosure is to be considered as an exemplification of the principles of the invention and is not intended to limit the broad aspects of the invention to the embodiments illustrated. It will be understood that the invention may be embodied in other specific forms without departing from the spirit or central characteristics thereof. The present embodiments, therefore, are to be considered in all respects as illustrative and not restrictive, and the invention is not to be limited to the details given herein.

The elements of the small-volume nebulizer and elements of a valve system are described further in the '397 Patent, which may be referred to for further understanding of the present disclosure. This reference also discusses benefits associated with a breath-actuated valve application (e.g. reducing medicine waste during exhalation, etc.) and additional physiotherapy associated with a flow restrictor in the T-connector.

Figure 1:
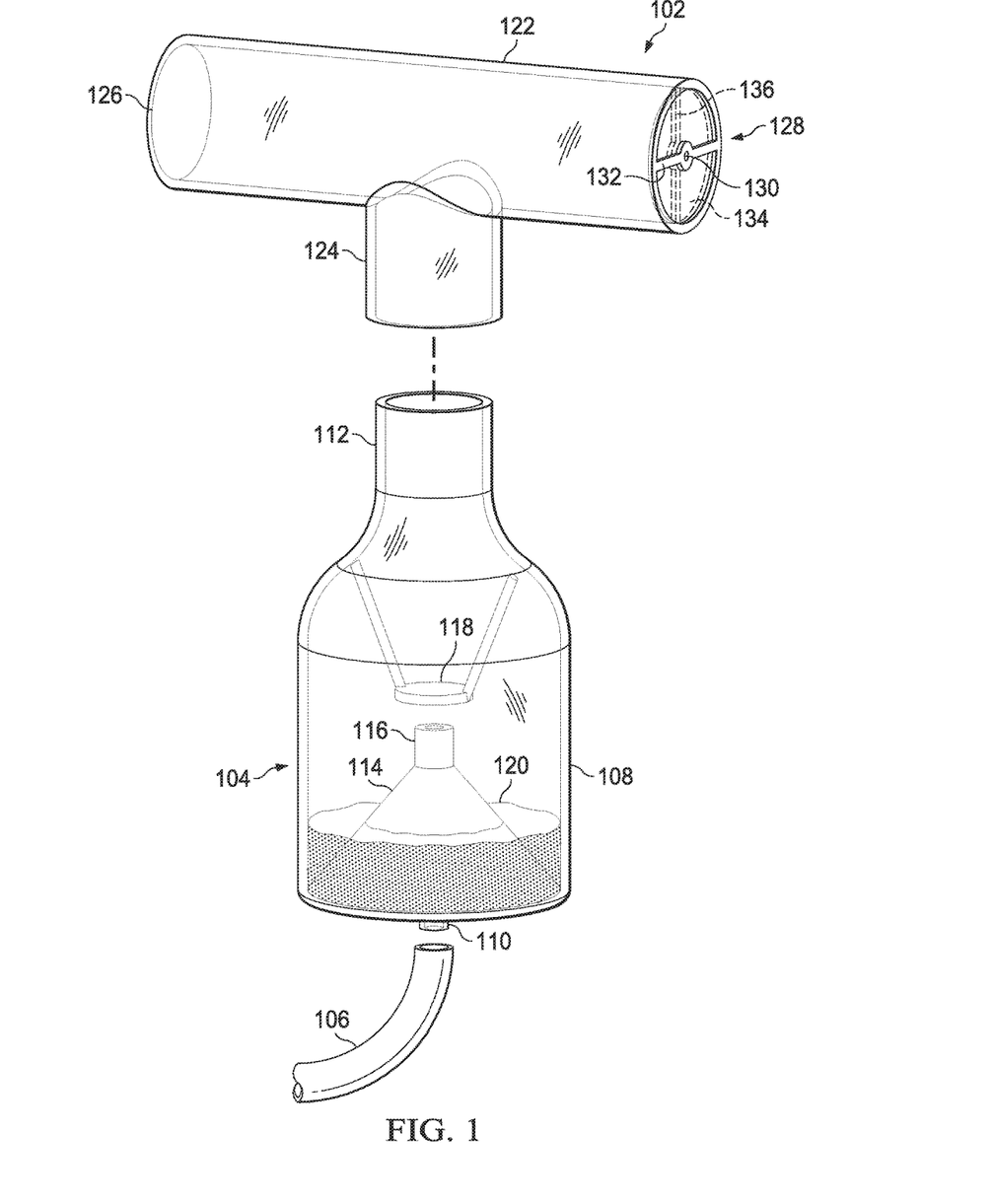
FIG. 1 is a perspective view of an embodiment of a T-connector having a flow controlled valve and a nebulizer.

FIG. 1 illustrates an embodiment of a small volume nebulizer assembly including a T-connector 102 and a small-volume nebulizer 104. Components may be fabricated by injection molding a plastic compound, such as a polypropylene or other plastic compound with appropriate properties for housing medication and fabricating a nebulizer. The small-volume nebulizer 104 may be comprised of a housing or body 108 containing a unit-dose of medication 120, a siphon 114, a jet 116, a baffle 118, an outlet port 112 and an inlet port 110 that connects to a gas source tube 106. In some embodiments, the housing 108 may comprise a housing top and a housing bottom connected at a housing seal.

The nebulizer 104 may be a pre-filled nebulizer such as the nebulizers discussed in U.S. Pat. No. 9,849,254 and the '397 Patent. These patents are both incorporated herein for reference.

The T-connector 102 includes tube with two ends referred to as horizontal tube 122. In this embodiment, a vertical tube 124 is located between the two ends of the horizontal tube 122. The vertical tube 124 is configured to attach to the nebulizer 104's output port 112 and may be referred to as a nebulizer port.

The horizontal tube 122's first end includes a front port 126 configured to provide a patient interface. In some embodiments, the front port 126 may comprise a mouthpiece. In other embodiments, the front port 126 may be connectable to a mouthpiece, mask or other patient interface component. On the opposite end of the horizontal tube 122 is a flow controlled valve 128, which operates as a flow restrictor in at least one airflow direction. In some embodiments, the second end of the horizontal tube 122 having the flow controlled valve 128 may have a port for connection to other components. For example, the horizontal tube 122 may be connected in-line with a ventilator circuit.

In this embodiment, the flow controlled valve 128 includes hole 130, exterior strut 132, interior strut 136 and valve gate 134. The hole 130 passes through the exterior strut 132, the interior strut 136 and the valve gate 134 and allows air to flow in both directions through the flow controlled valve 128.

The exterior strut 132 and the interior strut 136 are on opposite sides of the valve gate 134 and hold the valve gate 134 in place. In some embodiments, the valve gate 134 is attached to one strut along its length and only held by the second strut at the central overlap between the struts. For example, the valve gate 134 may be attached to the exterior strut 132 from one end to the strut 132's opposite end. The struts 132, 136 are structural supports for the valve gate 134. Some embodiments may include an alternative structural support.

The valve gate 134 is able to flex outward around the exterior strut 132 to allow air outflow from the T-connector 102. In contrast, the interior strut 136 and the attachment to the exterior strut 132 prevent or significantly limit the valve gate 134's ability to flex inward. During use, air will pass outward through the hole 130 and the openings created by the valve gate 134 flexing outward. The air will pass inward through hole 130, but will be prevented or significantly limited from passing around the valve gate 134. Thus, a user can exhale through the T-connector 102 with less work than the user will need to inhale through the T-connector 102.

As another example, the valve gate 134 may be attached to the interior strut 136 from one end to the strut 136's opposite end. The valve gate 134 is able to flex inward around the interior strut 136 to allow air to flow into the T-connector 102. In contrast, the exterior strut 132 and the attachment to the interior strut 136 prevent or significantly limit the valve gate 134's ability to flex outward. During use, air will pass inward through the hole 130 and the openings created by the valve gate 134 flexing inward. Air will pass outward through hole 130, but will be prevented or significantly limited from passing around the valve gate 134. Thus, a user can inhale through the T-connector 102 with less work than the user will need to exhale through the T-connector 102.

In some embodiments, the valve gate 134 is configured to open and close based on a user's inspiration and expiration. The valve gate 134 may be made of an appropriate substance, such as neoprene, which has the qualities of being lightweight, flexible, and impervious to liquid. In some embodiments, the valve gate 134 may be selected for specific flexibility qualities such that a user must apply a sufficient force to cause the valve gate 134 to open.

Figure 2:
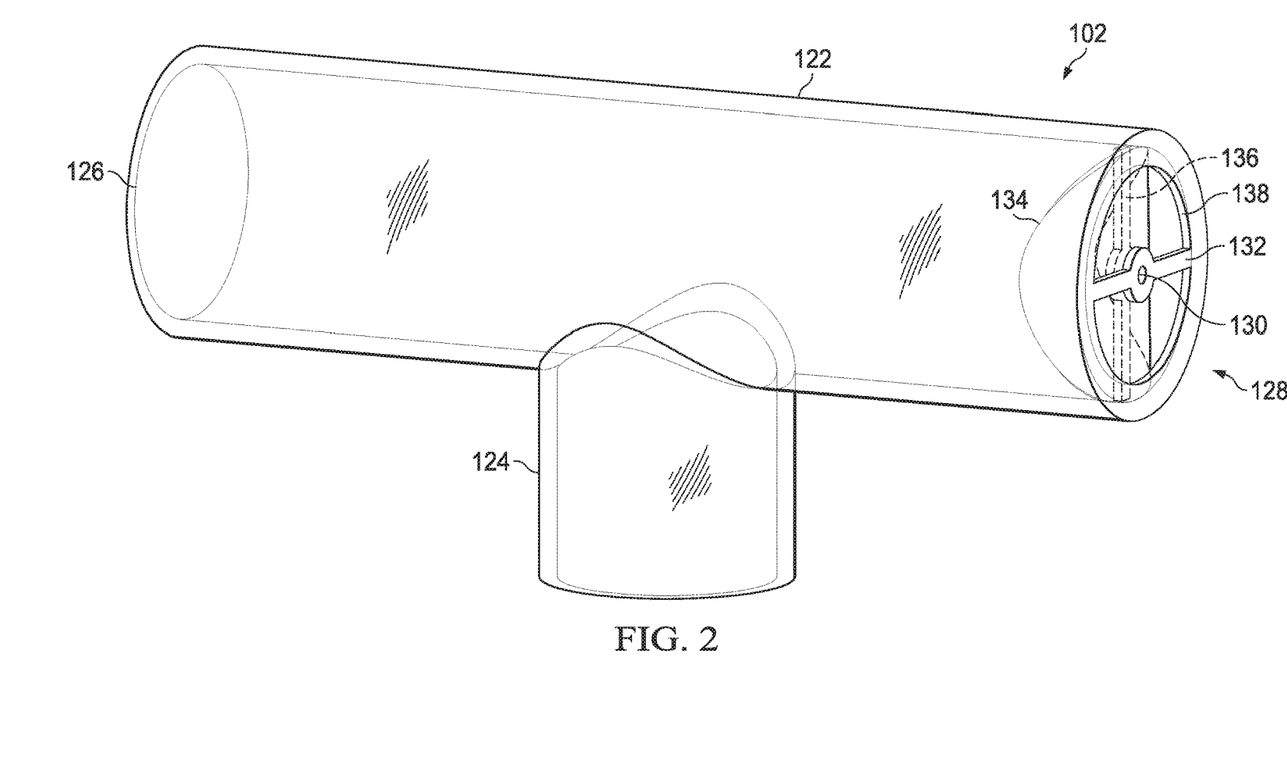
FIG. 2 is a perspective view of an embodiment of the T-connector having a flow controlled valve.
Figure 3:
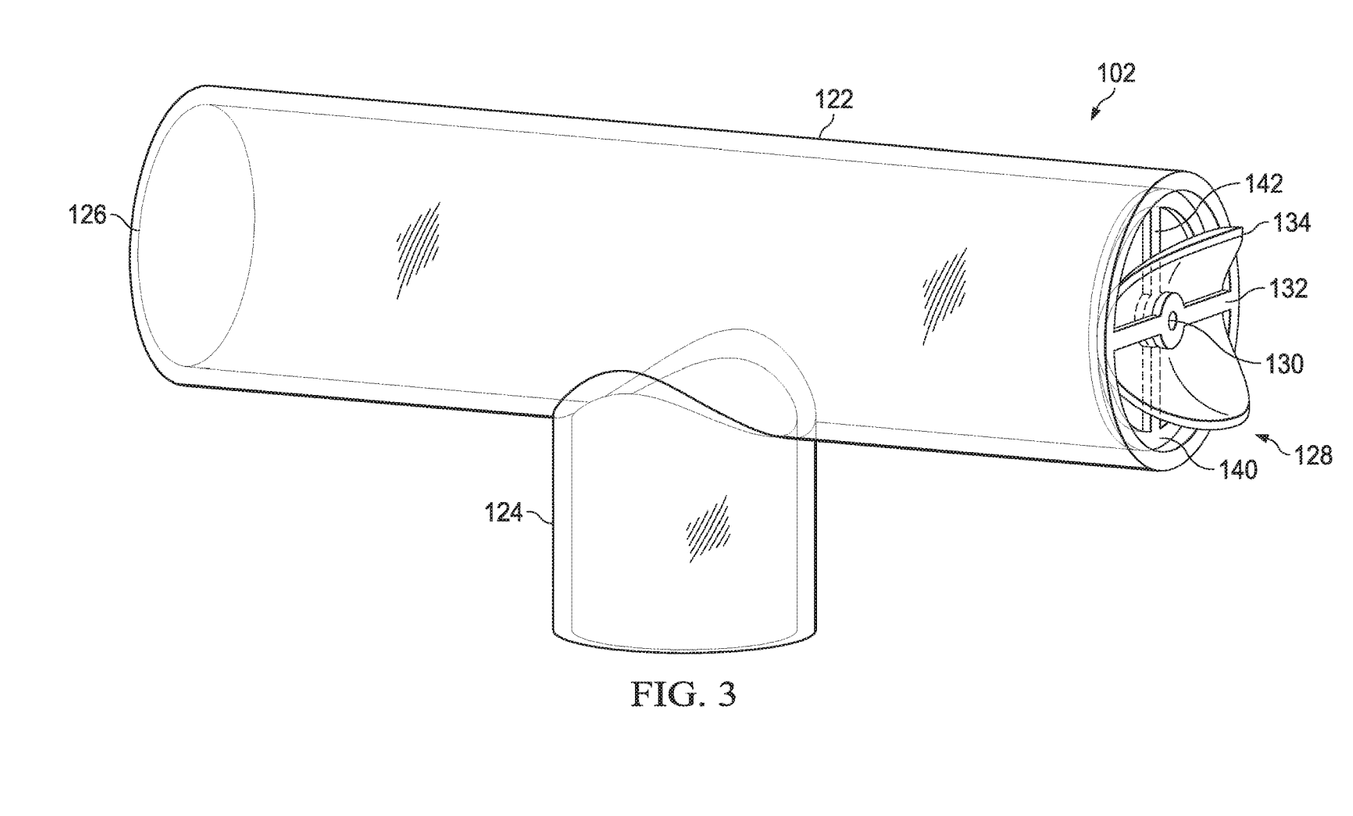
FIG. 3 is a perspective view of another embodiment of the T-connector having a flow controlled valve.

FIG. 2 shows an embodiment of T-connector 102 with horizontal tube 122 and vertical tube 124. The horizontal tube 122 includes the front port 126 on one end and a flow controlled valve 128 on the opposite end. The flow controlled valve 128 includes hole 130, exterior strut 132, interior strut 136 and valve gate 134 which is shown in an open position. The hole 130 passes through the exterior strut 132, the interior strut 136 and the valve gate 134 and allows air to flow in both directions through the flow controlled valve 128. The valve gate 134 is attached between the exterior strut 132 and the interior strut 136. In some embodiments, only one strut may be included with a tab, center pivot or other component to attach the valve gate 134 to the strut. In such embodiments, the tab or other component may include hole 130.

In this embodiment, the flow controlled valve 128 also includes valve seat 138 which is a ring extending inward within the inner wall of the horizontal tube 122 around exterior edge of the horizontal tube 122's second end. When the valve gate 134 is in a closed position, the valve gate 134's outer edge closes against the valve seat 138. The flow controlled valve 128 is located adjacent to the edge of the horizontal tube 122's second end. In some embodiments, the flow controlled valve 128 may be located further within the horizontal tube 122 with the vertical tube 124 between the flow controlled valve 128 and the front port 126.

Figure 4:
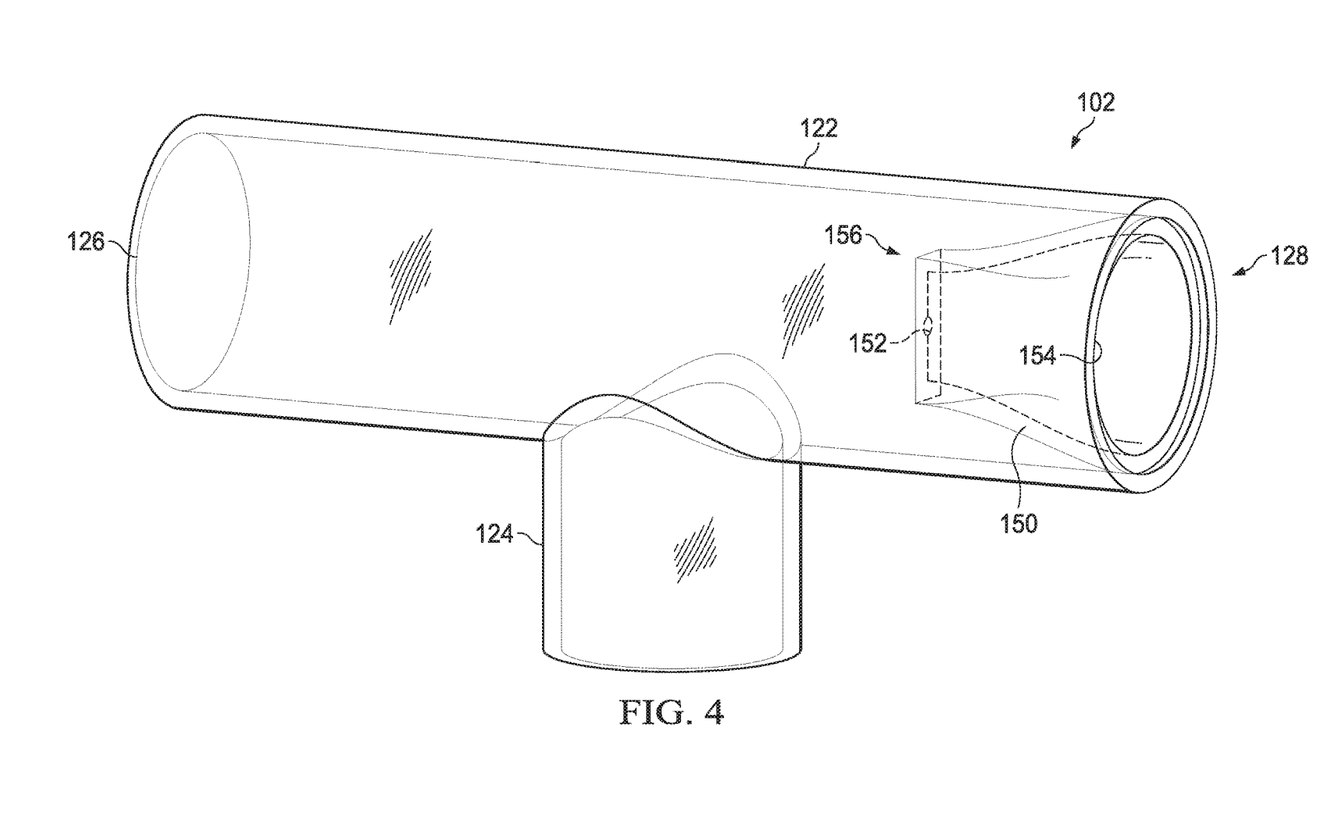
FIG. 4 is a perspective view of another embodiment of the T-connector having a flow controlled valve.
Figure 5:
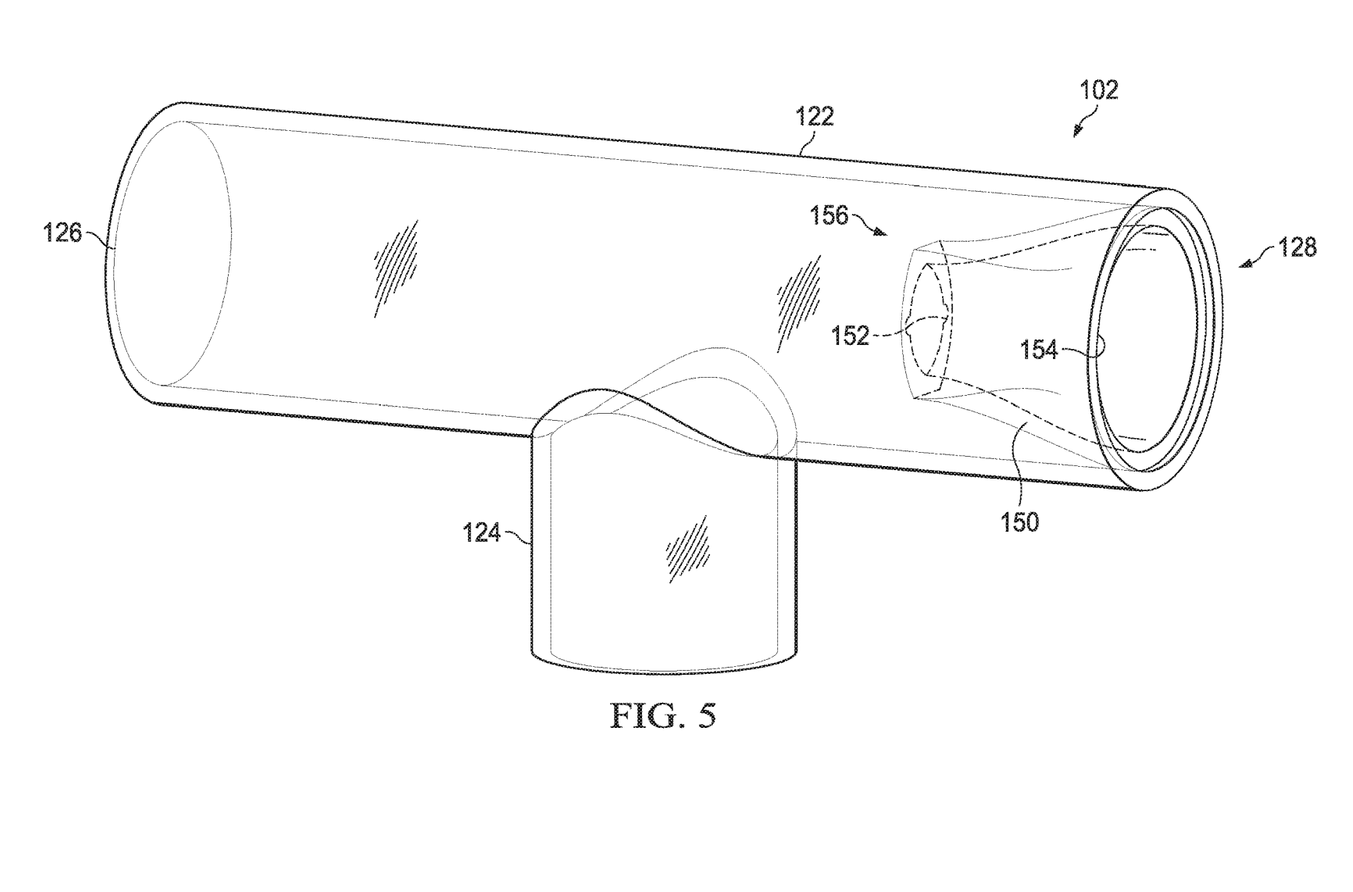
FIG. 5 is a perspective view of the T-connector having a flow controlled valve from FIG. 4 with the valve open.

During respiratory operation, the user inhales through a patient interface on the front port 126 wherein air is drawn through the hole 130 and the valve gate 134 opens around the interior strut 136, allowing air through the openings between the struts 132, 136 and the valve seat 138, and around the valve gate 134 to the user. Air is also drawn through the vertical tube 124. When a nebulizer 104 is attached to the vertical tube 124, aerosolized medicine is pulled through the vertical tube 124 into the user's lungs. When the user exhales, the valve gate 134 shuts against the valve seat 138, preventing air from passing through the openings around the struts 132, 136. Exhaled air only exits the horizontal tube 122's second end through hole 130. In this embodiment, the T-connector 102 creates a higher flow resistance during exhalation than inhalation.

The valve gate 134 may be configured to open and close based on a user's inspiration and expiration. For example, the valve gate 134 may be designed to be more flexible for a user with weaker lungs than a user with stronger lungs. The valve gate 134 may be made of an appropriate substance, such as neoprene, which has the qualities of being lightweight, flexible, and impervious to liquid. In some embodiments, the valve gate 134 may be selected for specific flexibility qualities such that a user must apply a sufficient force to cause the valve gate 134 to open. In some embodiments, the valve gate 134 is in a normally closed position until forced open by a drop in pressure within horizontal tube 122 corresponding to a user's inspiration. During expiration, the valve gate 134 returns to a closed position creating a seal against the valve seat 138.

In some embodiments, the flow controlled valve 128 restricts airflow in both directions. For example, when the valve gate 134 is in the open position, the openings around the struts 132,136 may also limit the airflow into the horizontal tube 122, choking or limiting the user's inspiratory airflow. In such an embodiment, the flow controlled valve 128 may facilitate physiotherapy during inspiration and expiration. In some embodiments, the flow controlled valve 128 is configured to facilitate a first flow restriction through the hole 130 and a second flow restriction through the hole 130 and the additional openings created by the valve gate 134 opening.

FIG. 3 shows an embodiment of T-connector 102 similar to the T-connector 102 in FIG. 2 with horizontal tube 122 and vertical tube 124. The horizontal tube 122 also includes the front port 126 on one end and a flow controlled valve 128 on the opposite end. Like FIG. 2, the flow controlled valve 128 includes hole 130, exterior strut 132 and valve gate 134 which is shown in an open position. In this embodiment, the flow controlled valve 128 includes a valve seat 140, which is a ring extending inward within the inner wall of the horizontal tube 122's second end. The flow controlled valve 128 also includes an interior strut 142 extending from one side of valve seat 140 to an opposite side of valve seat 140. When the valve gate 134 is in a closed position, the valve gate 134's outer edge closes against the valve seat 140.

The valve seat 140 and interior strut 142 are on the valve gate 134's opposite side from the exterior strut 132. In this embodiment, the exterior strut 132 is at the edge of the horizontal tube 122's opposite end. In some embodiments, the flow controlled valve 128 may be located further within the horizontal tube 122 between the vertical tube 124 and the second end opposite from the front port 126.

The hole 130 passes through the exterior strut 132, the interior strut 142 and the valve gate 134 and allows air to flow in both directions through the flow controlled valve 128. In some embodiments, the valve gate 134 is held in place between the exterior strut 132 and the interior strut 142. The valve gate 134 may be attached to the exterior strut 132 or the interior strut 142. In some embodiments, only one strut may be included with a tab, center pivot or other component to attach the valve gate 134 to the strut. In such embodiments, the tab or other component may include the hole 130.

During respiratory operation, the user inhales through a patient interface on the front port 126 wherein air is only drawn through the horizontal tube 122's second end through hole 130. The valve gate 134 shuts against the valve seat 140 preventing air from passing through the openings around the struts 132, 142 during inhalation. Air is also drawn through the vertical tube 124. When a nebulizer 104 is attached to the vertical tube 124, aerosolized medicine is pulled through the vertical tube 124 into the user's lungs. When the user exhales, air is pushed out through hole 130 and the valve gate 134 opens around the exterior strut 132 allowing air through the openings between the struts 132, 142 and the valve seat 140 and around the valve gate 134 to the ambient or other exhalation outlet. In this embodiment, the T-connector 102 creates a higher flow resistance during inhalation than exhalation.

The valve gate 134 may be configured to open and close based on a user's inspiration and expiration. For example, the valve gate 134 may be designed to be more flexible for a user with weaker lungs than a user with stronger lungs. The valve gate 134 may be made of an appropriate substance, such as neoprene, which has the qualities of being lightweight, flexible, and impervious to liquid. In some embodiments, the valve gate 134 may be selected for specific flexibility qualities such that a user must apply a sufficient force to cause the valve gate 134 to open. In some embodiments, the valve gate 134 is in a normally closed position until forced open by an increased pressure within horizontal tube 122 corresponding to a user's expiration. During inhalation, the valve gate 134 returns to a closed position creating a seal against the valve seat 140.

In some embodiments, the flow controlled valve 128 restricts airflow in both directions. For example, when the valve gate 134 is in the open position, the openings around the struts 132,136 may also limit the airflow out of the horizontal tube 122, choking or limiting the user's expiratory airflow. In such an embodiment, the flow controlled valve 128 may facilitate physiotherapy during inspiration and expiration. In some embodiments, the flow controlled valve 128 is configured to facilitate a first flow restriction through the hole 130 and a second flow restriction through the hole 130 and the additional openings created by the valve gate 134 opening.

FIGS. 4 and 5 show an embodiment of T-connector 102 with horizontal tube 122 and vertical tube 124. The horizontal tube 122 includes the front port 126 on one end and another embodiment of flow controlled valve 128 on the opposite end. In this embodiment, the flow controlled valve 128 is a duckbill valve 150 which includes hole 152 in the duckbill valve 150's lips 156. In this embodiment, the duckbill valve 150's open end 154 is adjacent to the horizontal tube 122's second end opposite the front port 126, and the lips 156 are within the horizontal tube 122 and directed toward the front port 126. FIG. 4 shows the lips 156 in a closed state, and FIG. 5 shows lips 156 in an open state.

The hole 152 is fixed in the lips 156 and configured to allow air to flow in both directions through the flow controlled valve 128 whether the lips 156 are open or closed. In this embodiment, the hole 152 is made by corresponding cutouts on each of the lips 156 that form an opening fixed in the lips 156 and structured to prevent the hole 152 from closing. In some embodiments, the hole 152 may be located in the duckbill valve 150's side walls, which are between the lips 156 and the open end 154. While a single hole 152 is shown, some embodiments may include multiple holes 152 located in the duckbill valve 150. For example, additional holes 152 may be created above or below hole 152 along the lip 156's seam. For another example, holes 152 may be in the duckbill valve 150's side walls.

The duckbill valve 150 may be connected to the horizontal tube 122 by adhesive, sonic welding, compression connections, friction connections, fitted connections or other attachment methods. In some embodiments, the connection may allow the duckbill valve 150 to be removable. For example, the duckbill valve 150 may be attached by a threaded connection to the horizontal tube 122.

The flow controlled valve 128 is located adjacent to the edge of the horizontal tube 122's second end. In some embodiments, the flow controlled valve 128 may be located further within the horizontal tube 122 between the vertical tube 124 and the second end of horizontal tube 122 from the front port 126.

During respiratory operation, the user inhales through a patient interface on the front port 126 wherein air is drawn through the hole 152 and the lips 156 open, as shown in FIG. 5, allowing more air through the duckbill valve 150 to the user. Air is also drawn through the vertical tube 124. When a nebulizer 104 is attached to the vertical tube 124, aerosolized medicine is pulled through the vertical tube 124 into the user's lungs. When the user exhales, the duckbill valve 150's lips 156 shut, as shown in FIG. 4, limiting exhaled air to only exiting the horizontal tube 122's second end through hole 152. In this embodiment, the T-connector 102 creates a higher flow resistance during exhalation than inhalation.

The duckbill valve 150 may be configured to open and close based on a user's inspiration and expiration. For example, the duckbill valve 150 may be designed to be more flexible for a user with weaker lungs than a user with stronger lungs. The duckbill valve 150 may be made of an appropriate substance, such as neoprene, which has the qualities of being lightweight, flexible, and impervious to liquid. In some embodiments, the duckbill valve 150 may be selected for specific flexibility qualities such that a user must apply a sufficient force to cause the duckbill valve 150 to open. In some embodiments, the duckbill valve 150's lips 156 are normally in a closed position until forced open by a drop in pressure within horizontal tube 122 corresponding to a user's inspiration. During expiration, the duckbill valve 150's lips 156 return to a closed position.

In some embodiments, the flow controlled valve 128 restricts airflow in both directions. For example, when the duckbill valve 150 is in the open position, the lips 156 may also limit the airflow into the horizontal tube 122, choking or limiting the user's inspiratory airflow. In such an embodiment, the flow controlled valve 128 may facilitate physiotherapy during inspiration and expiration. In some embodiments, the flow controlled valve 128 is configured to facilitate a first flow restriction through the hole 152 and a second flow restriction through the hole 152 and the additional space created by the duckbill valve 150 opening.

Figure 6:
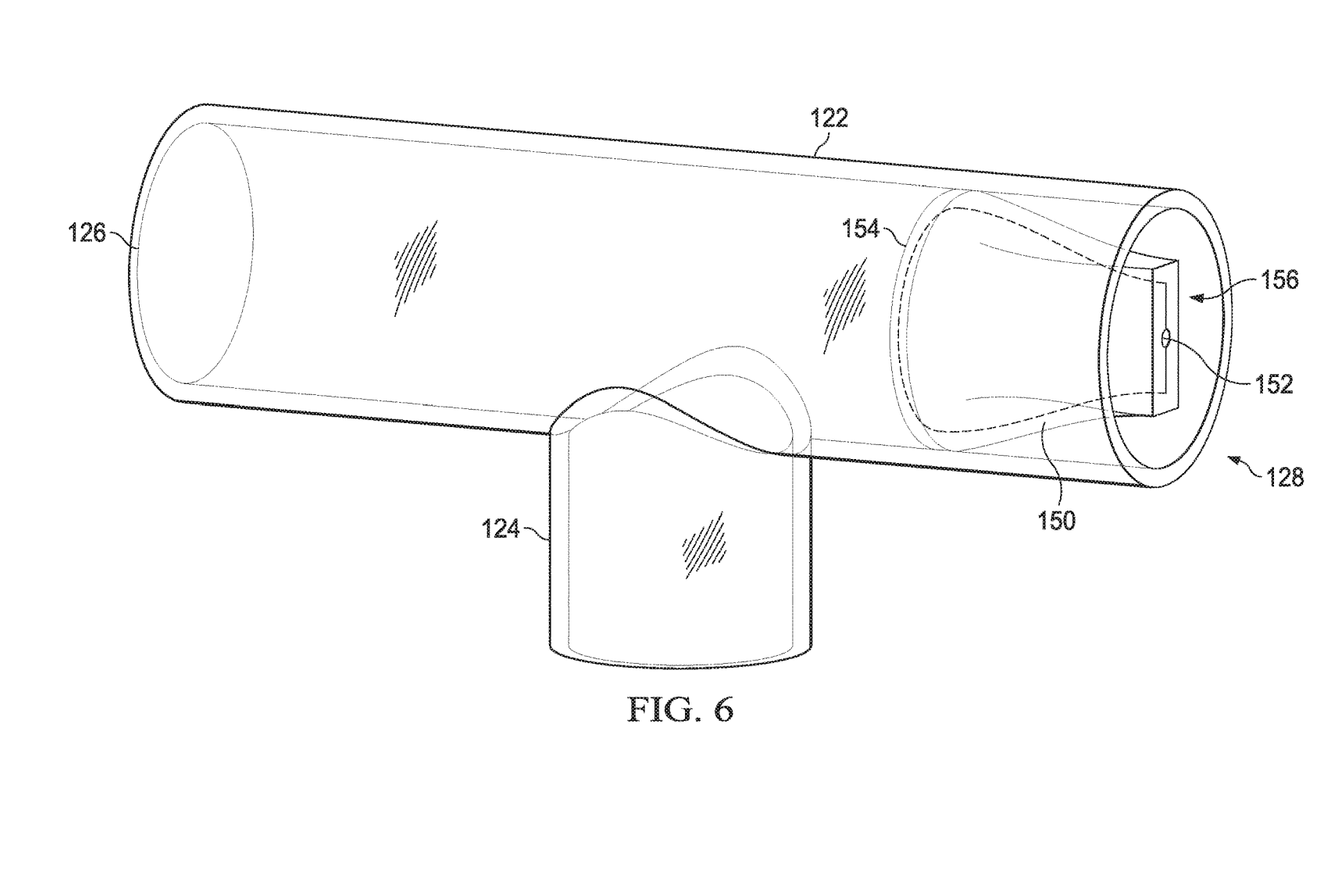
FIG. 6 is a perspective view of another embodiment of the T-connector having a flow controlled valve.
Figure 7:
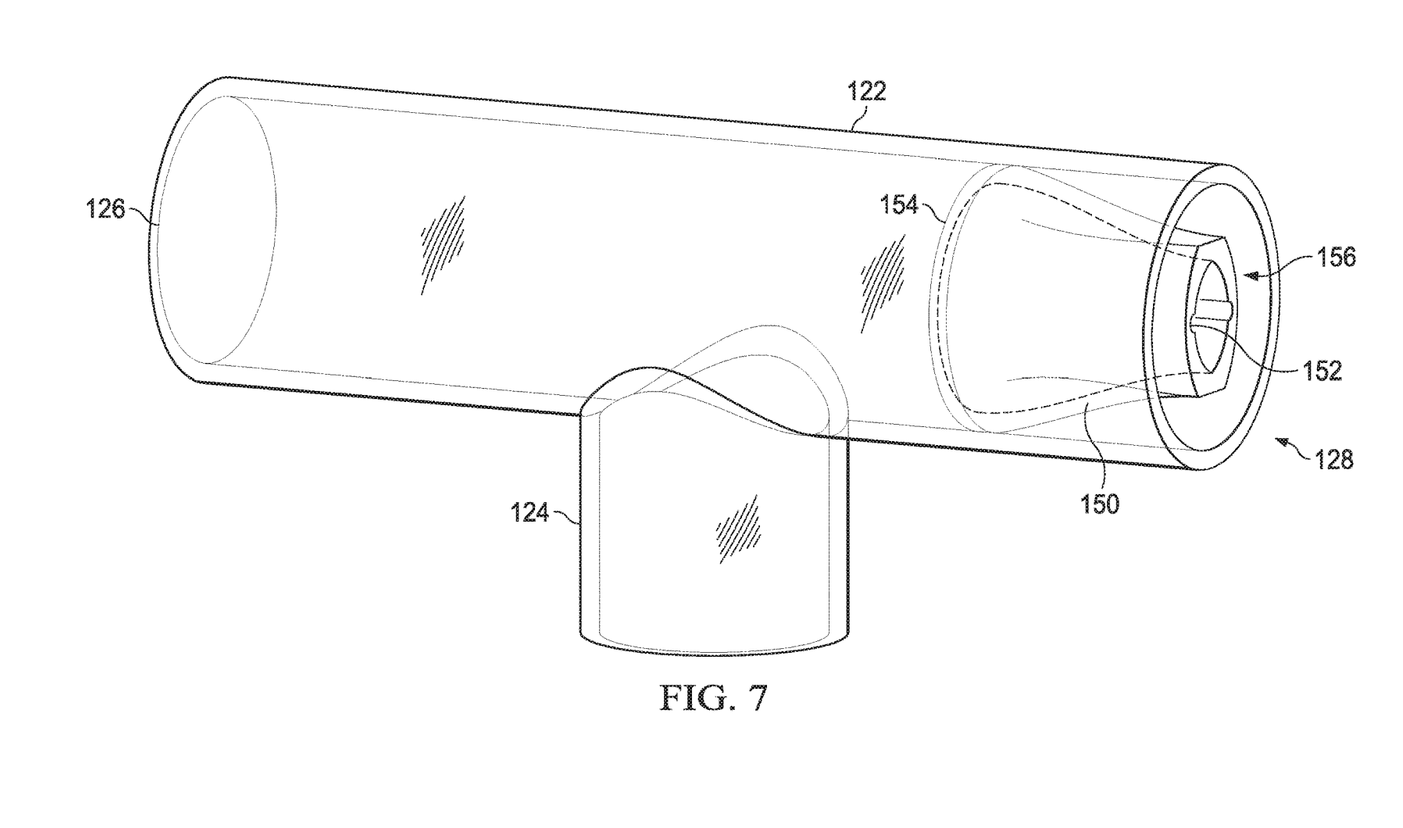
FIG. 7 is a perspective view of the T-connector having a flow controlled valve from FIG. 6 with the valve open.

FIGS. 6 and 7 also show an embodiment of T-connector 102 with horizontal tube 122 and vertical tube 124. The horizontal tube 122 includes the front port 126 on one end and another embodiment of flow controlled valve 128 on the opposite end. In this embodiment, the flow controlled valve 128 is a duckbill valve 150 which includes hole 152 in the duckbill valve 150's lips 156. In this embodiment, the duckbill valve 150's open end 154 is recessed within the horizontal tube 122's second end opposite the front port 126 and the lips 156 are directed to the horizontal tube 122's second end. FIG. 6 shows the lips 156 in a closed state and FIG. 7 shows lips 156 in an open state.

The hole 152 is fixed in the lips 156 and configured to allow air to flow in both directions through the flow controlled valve 128 whether the lips 156 are open or closed. In this embodiment, the hole 152 is made by corresponding cutouts on each of the lips 156 that form an opening fixed in the lips 156 and structured to prevent the hole 152 from closing. In some embodiments, the hole 152 may be located in the duckbill valve 150's side walls, which are between the lips 156 and the open end 154. While a single hole 152 is shown, some embodiments may include multiple holes 152 located in the duckbill valve 150. For example, additional holes 152 may be created above or below hole 152 along the lip 156's seam. For another example, holes 152 may be in the duckbill valve 150's side walls.

The duckbill valve 150 may be connected to the horizontal tube 122 by adhesive, sonic welding, compression connections, friction connections, fitted connections or other attachment methods. In some embodiments, the connection may allow the duckbill valve 150 to be removable. For example, the duckbill valve 150 may be attached by a threaded connection to the horizontal tube 122.

The flow controlled valve 128 is located with the lips 156 adjacent to the edge of the horizontal tube 122's second end. In some embodiments, the flow controlled valve 128 may be located further within the horizontal tube 122 between the vertical tube 124 and the second end of the horizontal tube 122 from the front port 126. In some embodiments, the open end 154 may be located adjacent to the edge of the horizontal tube 122's second end with a substantial portion of the duckbill valve 150 extending beyond the edge of the horizontal tube 122's second end.

During respiratory operation, the user inhales through a patient interface on the front port 126 wherein air is limited to entering the horizontal tube 122's second end through the hole 152 because the duckbill valve 150's lips 156 are closed, as shown in FIG. 6. Air is also drawn through the vertical tube 124. When a nebulizer 104 is attached to the vertical tube 124, aerosolized medicine is pulled through the vertical tube 124 into the user's lungs. When the user exhales, air escapes through the hole 152 and the lips 156 which open, as shown in FIG. 7, allowing more air to escape through the duckbill valve 150. In this embodiment, the T-connector 102 creates a higher flow resistance during inhalation than exhalation.

The duckbill valve 150 may be configured to open and close based on a user's inspiration and expiration. For example, the duckbill valve 150 may be designed to be more flexible for a user with weaker lungs than a user with stronger lungs. The duckbill valve 150 may be made of an appropriate substance, such as neoprene, which has the qualities of being lightweight, flexible, and impervious to liquid. In some embodiments, the duckbill valve 150 may be selected for specific flexibility qualities such that a user must apply a sufficient force to cause the duckbill valve 150 to open. In some embodiments, the duckbill valve 150's lips 156 are normally in a closed position until forced open by an increase in pressure within horizontal tube 122 corresponding to a user's expiration. During inhalation, the duckbill valve 150's lips 156 return to a closed position.

In some embodiments, the flow controlled valve 128 restricts airflow in both directions. For example, when the duckbill valve 150 is in the open position, the lips 156 may also limit the airflow out of the horizontal tube 122, choking or limiting the user's expiratory airflow. In such an embodiment, the flow controlled valve 128 may facilitate physiotherapy during inspiration and expiration. In some embodiments, the flow controlled valve 128 is configured to facilitate a first flow restriction through the hole 152 and a second flow restriction through the hole 152 and the additional space created by the duckbill valve 150 opening.

Figure 8:
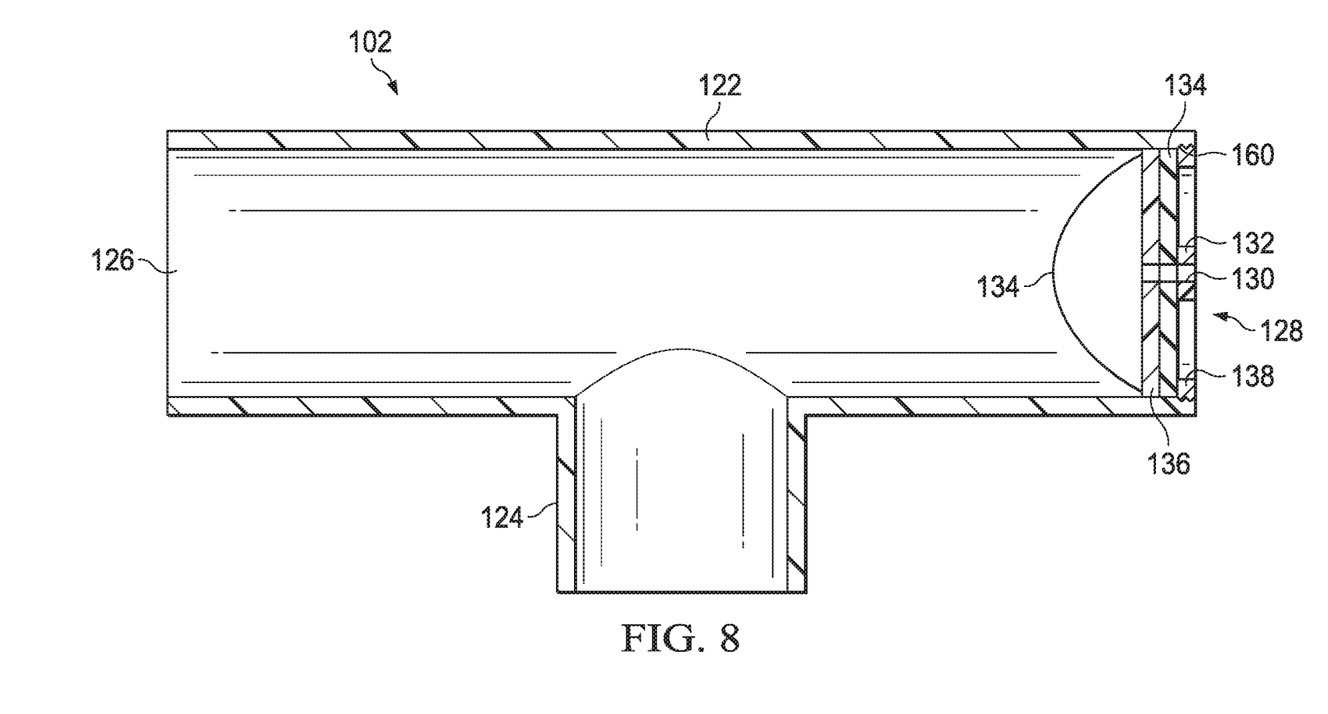
FIG. 8 is a cross-section view of the T-connector having a flow controlled valve which is open.

FIG. 8 shows a cross-section of an embodiment of T-connector 102 with horizontal tube 122 and vertical tube 124. This T-connector 102 is similar to the embodiment shown in FIG. 2 and described above. The horizontal tube 122 includes the front port 126 on one end and a flow controlled valve 128 on the opposite end. The flow controlled valve 128 includes hole 130, exterior strut 132, interior strut 136 and valve gate 134 which is shown in an open position. The hole 130 passes through the exterior strut 132, the interior strut 136 and the valve gate 134 and allows air to flow in both directions through the flow controlled valve 128. In some embodiments, only one strut may be included with a tab, center pivot or other component to attach the valve gate 134 to the strut. In such embodiments, the tab or other component may include hole 130.

In this embodiment, the flow controlled valve 128 is a separate component that is configured to connect to the horizontal tube 122. Connector 160 located on the outer edge of the flow controlled valve 128 is designed to the horizontal tube 122's second end. The connector 160 may facilitate a removable connection such as a threaded connection, a friction or snap fit connection, a fitted connection or other removable connection. In some embodiments, the connector 160 may facilitate a permanent or semi-permanent connection, such as a locking connection, an adhesive connection, sonic welding or other permanent or semi-permanent connection.

The flow controlled valve 128 also includes valve seat 138 which is a ring extending inward from the connector 160 within the inner wall of the tube 122 around exterior edge of the horizontal tube 122's second end. When the valve gate 134 is in a closed position, the valve gate 134's outer edge closes against the valve seat 138. The flow controlled valve 128 is located adjacent to the edge of the horizontal tube 122's second end. In some embodiments, the flow controlled valve 128 may be located further within the horizontal tube 122 between the vertical tube 124 and the second end of the horizontal tube 122 opposite from the front port 126.

When the flow controlled valve 128's connector 160 is attached to the horizontal tube 122's second end, this T-connector 102 operates in the same manner as the embodiment in FIG. 2. As the user inhales through a patient interface on the front port 126, air is drawn through the hole 130 and the valve gate 134 opens around the interior strut 136, allowing air through the openings between the struts 132, 136 and the valve seat 138 around the valve gate 134 to the user. Air is also drawn through the vertical tube 124. When a nebulizer 104 is attached to the vertical tube 124, aerosolized medicine is pulled through the vertical tube 124 into the user's lungs. When the user exhales, the valve gate 134 shuts against the valve seat 138, preventing air from passing through the openings around the struts 132, 136. Exhaled air only exits the horizontal tube 122's second end through hole 130. In this embodiment, the T-connector 102 creates a higher flow resistance during exhalation than inhalation.

The valve gate 134 may be configured to open and close based on a user's inspiration and expiration. For example, the valve gate 134 may be designed to be more flexible for a user with weaker lungs than a user with stronger lungs. The valve gate 134 may be made of an appropriate substance, such as neoprene, which has the qualities of being lightweight, flexible, and impervious to liquid. In some embodiments, the valve gate 134 may be selected for specific flexibility qualities such that a user must apply a sufficient force to cause the valve gate 134 to open. In some embodiments, the valve gate 134 is in a normally closed position until forced open by a drop in pressure within horizontal tube 122 corresponding to a user's inspiration. During expiration, the valve gate 134 returns to a closed position creating a seal against the valve seat 138.

In some embodiments, the flow controlled valve 128 restricts airflow in both directions. For example, when the valve gate 134 is in the open position, the openings around the struts 132, 136 may also limit the airflow into the horizontal tube 122, choking or limiting the user's inspiratory airflow. In such an embodiment, the flow controlled valve 128 may facilitate physiotherapy during inspiration and expiration. In some embodiments, the flow controlled valve 128 is configured to facilitate a first flow restriction through the hole 130 and a second flow restriction through the hole 130 and the additional openings created by the valve gate 134 opening.

In some embodiments, the connector 160 may be configured to allow the flow controlled valve 128 to connect as shown or alternatively wherein the valve gate 134 opens outward.

In some embodiments, the flow controlled valve 128 may be used for other environments or structures.

During manufacture, the T-connector 102 and the nebulizer 104 may be sterilized. In some embodiments, the T-connector 102 may be connected to the nebulizer 104 that is pre-filled with a unit dose of medication 120. The assembly may be sealed with an input port sealing component and an internal seal in the nebulizer 104's output port 112 or vertical tube 124. The T-connector 102 may also be sterilized. In some embodiments, a medication label may be affixed to the assembly indicating the medicine and dosage, as well as other usage and medication information.

During operation, high-pressure gas is introduced into the input port 110 from gas source tube 106 which is connected prior to use. Gas flows into the input port 110 at an appropriate flow rate, typically ranging from 6 to 10 liters per minute, and is directed through jet 116, which has a narrowed orifice in order to accelerate the velocity of the gas. One skilled in the art will recognize that the gas will typically be oxygen, air and/or another gas and remain within the scope and spirit of the disclosure. In some embodiments, the gas will be provided by a compressed gas source. As the velocity increases, pressure within siphon 114 drops, creating a suction, which serves to entrain medication 120. Medication 120 is hurled as spray against baffle 118.

Baffle 118 is a surface that causes large particles to fall out of suspension, thus reducing the overall average particle size of the aerosol. As the user breathes inward, the aerosolized medicine 120 passes through the vertical tube 124 into the horizontal tube 122 and to the patient through the front port 126.

In some embodiments, a respiratory patient interface with a flow controlled valve includes a patient interface component having a nebulizer port and a tube. The tube has a patient interface port and a valve port located at opposite ends of the tube and the nebulizer port is between the patient interface port and the flow controlled valve. The nebulizer port is operable to connect to a nebulizer. The flow controlled valve is located in the valve port and includes a hole that passes through the flow controlled valve, allowing airflow through the hole in both a first direction and a second direction. The flow controlled valve also includes a one-way valve that has an open configuration that allows additional airflow and a closed configuration that prevents the additional airflow through the flow controlled valve. The one-way valve is in the open configuration when the air moves in the first direction and is in the closed configuration when the air moves in the second direction.

Embodiments of the one-way valve may include a valve gate operable to move between the open configuration and the closed configuration, a valve gate support and a valve seat. The valve gate is attached to the valve gate support and the valve gate creates a seal against the valve seat in the closed configuration. In such embodiments, the hole may pass through the valve gate and the valve gate support.

In some embodiments, the one-way valve comprises a duckbill valve with lips operable to move between the open configuration and the closed configuration. In such embodiments, the hole may be defined by fixed corresponding hole portions in the lips.

Some embodiments have a flow controlled valve assembly including a tube having a first port and a second port located at opposite ends of the tube and a flow controlled valve in the second port. The flow controlled valve includes a valve gate operable to move between an open configuration and a closed configuration, a valve gate support, wherein the valve gate is attached to the valve gate support, a valve seat, wherein the valve gate creates a seal against the valve seat in the closed configuration, an opening within the valve seat, and a hole that passes through the valve gate and the valve gate support. The valve gate may control airflow through the opening, wherein the airflow passes through the opening when the valve gate is in an open configuration and the opening is shut when the valve gate is in a closed configuration. The air may pass through the hole in both a first direction and a second direction. The valve gate may be in the open configuration when the air moves in the first direction and the airflow passes through the opening and the hole, and the valve gate may be in the closed configuration when the air moves in the second direction and the airflow passes through the hole while the opening is shut.

In some embodiments, the air moves from outside the tube to inside the tube through the flow controlled valve in the first direction and the air moves from inside the tube to outside the tube through the flow controlled valve in the second direction.

The air moves from inside the tube to outside the tube through the flow controlled valve in the first direction and the air moves from outside the tube to inside the tube through the flow controlled valve in the second direction in some embodiments.

The tube may be a horizontal tube of a T-connector for a nebulizer and the first port may be a patient interface port. In some embodiments, the air moves in the first direction during inhalation and the air moves in the second direction during exhalation. In other embodiments, the air moves in the first direction during exhalation and the air moves in the second direction during inhalation.

In some embodiments, the valve gate support comprises a first strut extending from one side of the valve seat to an opposite side of the valve seat. The valve gate support may include a second strut on an opposite side of the valve gate, and the valve gate may be held between the first strut and the second strut.

Some embodiments include a connector on an outside edge of the valve seat attaching the flow controlled valve to the second port of the tube. In such embodiments, the flow controlled valve may be removable from the tube.

In some embodiments, a flow controlled valve assembly includes a tube having a first port and a second port located at opposite ends of the tube and a flow controlled valve in the second port. The flow controlled valve may include a duckbill valve having an open end and lips with side walls extending from the open end to the lips which are operable to move between an open configuration forming an opening and a closed configuration shutting the opening, and a hole in the duckbill valve, wherein air passes through the hole in both a first direction and a second direction. The open end may attach to the second port of the tube. The lips are in the open configuration when the air moves in the first direction and the air passes through the opening and the hole, and the lips are in the closed configuration when the air moves in the second direction and the air passes through the hole while the opening is shut.

In some embodiments, the tube is a horizontal tube of a T-connector for a nebulizer and the first port is a patient interface port. The air may move in the first direction during inhalation and the air may move in the second direction during exhalation. In other embodiments, the air may move in the first direction during exhalation and the air may move in the second direction during inhalation.

In some embodiments, the lips have a first lip and a second lip and the hole includes a first hole portion fixed in the first lip and a second hole portion fixed in the second lip wherein the first hole portion and the second hole portion form the hole when the lips are in the closed configuration.

The invention being thus described and further described in the claims, it will be obvious that the same may be varied in many ways. Such variations are not to be regarded as a departure from the spirit and scope of the invention, and all such modifications as would be obvious to one skilled in the art are intended to be included within the scope of the apparatuses and methods described.

The invention claimed is:

1. A respiratory patient interface with a flow controlled valve comprising:
   a patient interface component including a nebulizer port and a tube having a patient interface port and a valve port located at opposite ends of the tube, wherein the nebulizer port is between the patient interface port and the flow controlled valve, and the nebulizer port is operable to connect to a nebulizer;
   the flow controlled valve is located in the valve port and comprises a hole that passes through the flow controlled valve, allowing airflow through the hole in both a first direction and a second direction and a one-way valve that has an open configuration that allows additional airflow and a closed configuration that prevents the additional airflow through the flow controlled valve, wherein the one-way valve is in the open configuration when air moves in the first direction and is in the closed configuration when the air moves in the second direction.

2. The respiratory patient interface with the flow controlled valve of claim 1, wherein the one-way valve comprises:
a valve gate operable to move between the open configuration and the closed configuration;
a valve gate support, wherein the valve gate is attached to the valve gate support; and
a valve seat, wherein the valve gate creates a seal against the valve seat in the closed configuration.

3. The respiratory patient interface with the flow controlled valve of claim 2, wherein the hole passes through the valve gate and the valve gate support.

4. The respiratory patient interface with the flow controlled valve of claim 1, wherein the one-way valve comprises a duckbill valve with lips operable to move between the open configuration and the closed configuration.

5. The respiratory patient interface with the flow controlled valve of claim 4, wherein the hole is defined by fixed corresponding hole portions in the lips.

6. A flow controlled valve assembly comprising:
a tube having a first port and a second port located at opposite ends of the tube;
a flow controlled valve in the second port comprising:
a valve gate operable to move between an open configuration and a closed configuration,
a valve gate support, wherein the valve gate is attached to the valve gate support,
a valve seat, wherein the valve gate creates a seal against the valve seat in the closed configuration,
an opening within the valve seat, wherein the valve gate controls airflow through the opening, wherein the valve gate is configured to allow the airflow to pass through the opening when the valve gate is in an open configuration and the opening is shut when the valve gate is in a closed configuration, and
a hole that passes through the valve gate and the valve gate support wherein the valve gate is configured to allow air to pass through the hole in both a first direction and a second direction;
wherein the valve gate is in the open configuration when the air moves in the first direction and the airflow passes through the opening and the hole, and wherein the valve gate is in the closed configuration when the air moves in the second direction and the airflow passes through the hole while the opening is shut.

7. The flow controlled valve assembly of claim 6, wherein the air moves from outside the tube to inside the tube through the flow controlled valve in the first direction and the air moves from inside the tube to outside the tube through the flow controlled valve in the second direction.

8. The flow controlled valve assembly of claim 6, wherein the air moves from inside the tube to outside the tube through the flow controlled valve in the first direction and the air moves from outside the tube to inside the tube through the flow controlled valve in the second direction.

9. The flow controlled valve assembly of claim 6, wherein the tube is a horizontal tube of a T-connector for a nebulizer and the first port is a patient interface port.

10. The flow controlled valve assembly of claim 9, wherein the flow controlled valve is configured to allow the air to move in the first direction during inhalation and allow the air to move in the second direction during exhalation.

11. The flow controlled valve assembly of claim 9, wherein the flow controlled valve is configured to allow the air to move in the first direction during exhalation and allow the air to move in the second direction during inhalation.

12. The flow controlled valve assembly of claim 6, wherein the valve gate support comprises a first strut extending from one side of the valve seat to an opposite side of the valve seat.

13. The flow controlled valve assembly of claim 12, wherein the valve gate support comprises a second strut on an opposite side of the valve gate, wherein the valve gate is held between the first strut and the second strut.

14. The flow controlled valve assembly of claim 6 further comprising a connector on an outside edge of the valve seat attaching the flow controlled valve to the second port of the tube.

15. The flow controlled valve assembly of claim 14, wherein the flow controlled valve is removable from the tube.

16. A flow controlled valve assembly comprising:
a tube having a first port and a second port located at opposite ends of the tube;
a flow controlled valve in the second port comprising:
a duckbill valve having an open end and lips with side walls extending from the open end to the lips, the open end attaches to the second port of the tube and the lips are operable to move between an open configuration forming an opening and a closed configuration shutting the opening, and a hole in the duckbill valve, wherein the duckbill valve is configured to allow air to pass through the hole in both a first direction and a second direction;
wherein the lips are in the open configuration when the air moves in the first direction and the air passes through the opening and the hole, and wherein the lips are in the closed configuration when the air moves in the second direction and the air passes through the hole while the opening is shut.

17. The flow controlled valve assembly of claim 16, wherein the tube is a horizontal tube of a T-connector for a nebulizer and the first port is a patient interface port.

18. The flow controlled valve assembly of claim 17, wherein the air moves in the first direction during inhalation and the air moves in the second direction during exhalation.

19. The flow controlled valve assembly of claim 17, wherein the air moves in the first direction during exhalation and the air moves in the second direction during inhalation.

20. The flow controlled valve assembly of claim 16, wherein the lips comprise a first lip and a second lip and the hole comprises a first hole portion fixed in the first lip and a second hole portion fixed in the second lip wherein the first hole portion and the second hole portion form the hole when the lips are in the closed configuration.

* * * * *

UNITED STATES PATENT AND TRADEMARK OFFICE
CERTIFICATE OF CORRECTION

PATENT NO. : 10,258,758 B1
APPLICATION NO. : 15/958369
DATED : April 16, 2019
INVENTOR(S) : Joseph Dee Faram et al.

Page 1 of 1

It is certified that error appears in the above-identified patent and that said Letters Patent is hereby corrected as shown below:

In the Specification

Column 1, Line 13: delete "disclose" and insert --discloses--

Column 3, Line 55: insert --a-- between "includes" and "tube"

In the Claims

Column 13, Line 40, Claim 6: delete "an" and insert --the--

Column 13, Line 42, Claim 6: delete "a" and insert --the--

Signed and Sealed this
Twenty-seventh Day of August, 2019

Andrei Iancu
*Director of the United States Patent and Trademark Office*